(12) United States Patent
Poecher et al.

(10) Patent No.: US 10,866,224 B2
(45) Date of Patent: *Dec. 15, 2020

(54) SYSTEM AND APPARATUS FOR USING A WIRELESS SMART DEVICE TO PERFORM FIELD CALCULATIONS

(71) Applicant: TSI, INCORPORATED, St. Paul, MN (US)

(72) Inventors: Arndt Poecher, Vadnais Heights, MN (US); Gerald M. Bark, White Bear Lake, MN (US); Rajagopala Menon, Shoreview, MN (US)

(73) Assignee: TSI, Incorporated, Shoreview, MN (US)

( * ) Notice: Subject to any disclaimer, the term of this patent is extended or adjusted under 35 U.S.C. 154(b) by 126 days.

This patent is subject to a terminal disclaimer.

(21) Appl. No.: 15/928,413

(22) Filed: Mar. 22, 2018

(65) Prior Publication Data

US 2019/0064132 A1 Feb. 28, 2019

Related U.S. Application Data

(63) Continuation of application No. 13/879,841, filed as application No. PCT/US2011/056943 on Oct. 19, 2011, now Pat. No. 9,933,401.

(Continued)

(51) Int. Cl.
| | |
|---|---|
| *G01N 33/00* | (2006.01) |
| *G01L 19/08* | (2006.01) |
| *G01D 1/18* | (2006.01) |
| *G01D 21/00* | (2006.01) |
| *F24F 3/16* | (2006.01) |
| *F24F 11/30* | (2018.01) |

(Continued)

(52) U.S. Cl.
CPC ............ *G01N 33/0009* (2013.01); *F24F 3/16* (2013.01); *F24F 11/30* (2018.01); *F24F 11/83* (2018.01);

(Continued)

(58) Field of Classification Search
CPC ...... G01N 33/0009; G01D 1/18; G01F 21/00; G01L 19/086; F24F 11/008;

(Continued)

(56) References Cited

U.S. PATENT DOCUMENTS

| | | |
|---|---|---|
| 5,018,875 A | 5/1991 | Cook |
| 5,136,285 A | 8/1992 | Okuyama |

(Continued)

OTHER PUBLICATIONS

T.J. Harpster, B. Stark, and K. Najafi, "A passive wireless integrated humidity sensor," Sensors and Actuators A 95 (2002) 100-107.

(Continued)

*Primary Examiner* — Edelmira Bosques
*Assistant Examiner* — Dana K Tighe
(74) *Attorney, Agent, or Firm* — Kagan Binder, PLLC (57) ABSTRACT

There is disclosed a system and apparatus for connecting remote and environmental sensors and other operating systems to a portable computing and communications device. The portable device configured to receive and process a set of data and transmit a response or message to at least the user on the quality of the data received. The portable device adapted to reconfigure the remote sensors or operating systems to produce a new set of data.

9 Claims, 8 Drawing Sheets

Related U.S. Application Data (60) Provisional application No. 61/394,597, filed on Oct. 19, 2010.

(51) Int. Cl.
*F24F 11/83* (2018.01)
*F24F 110/50* (2018.01)
*F24F 11/52* (2018.01)

(52) U.S. Cl.
CPC .............. *G01D 1/18* (2013.01); *G01D 21/00* (2013.01); *G01L 19/086* (2013.01); *F24F 11/52* (2018.01); *F24F 2110/50* (2018.01)

(58) Field of Classification Search
CPC .............. F24F 11/0017; F24F 11/0012; F24F 2011/0091; F24F 3/16; G01K 1/08; G01K 7/22
USPC .............. 454/239, 256, 370; 73/23.2, 28.01; 62/126, 127, 131; 374/183
See application file for complete search history.

(56) References Cited

U.S. PATENT DOCUMENTS

| | | | |
|---|---|---|---|
| 5,162,725 A | 11/1992 | Hodson et al. | |
| 5,260,875 A | 11/1993 | Tofte et al. | |
| 6,694,799 B2 | 2/2004 | Small | |
| 6,705,158 B1 | 3/2004 | Louden | |
| 7,096,125 B2 | 8/2006 | Padmanabhan et al. | |
| 7,302,313 B2 | 11/2007 | Sharp et al. | |
| 7,305,327 B2 | 12/2007 | Sper | |
| 7,788,294 B2 | 8/2010 | Van Wart et al. | |
| 2003/0007544 A1 | 1/2003 | Chang et al. | |
| 2007/0139183 A1 | 6/2007 | Kates | |
| 2007/0174152 A1* | 7/2007 | Bjornberg | G01C 15/00 705/28 |
| 2008/0117066 A1 | 5/2008 | Kononov et al. | |
| 2008/0213372 A1 | 9/2008 | Pastor et al. | |
| 2008/0281528 A1 | 11/2008 | Relle, Jr. | |
| 2009/0007706 A1 | 1/2009 | Hitt et al. | |
| 2009/0236432 A1 | 9/2009 | Malloy | |
| 2009/0311951 A1 | 12/2009 | Walkinshaw | |
| 2010/0036600 A1 | 2/2010 | Shinmyoh et al. | |
| 2010/0043529 A1 | 2/2010 | Wang et al. | |
| 2010/0070086 A1 | 3/2010 | Harrod et al. | |

OTHER PUBLICATIONS

International Search Report Issued in PCT/US2011/056943, dated Mar. 8, 2012, 2 pages.

Written Opinion issued in PCT/US2011/056943, dated Mar. 8, 2012, 7 pages.

\* cited by examiner

SYSTEM AND APPARATUS FOR USING A WIRELESS SMART DEVICE TO PERFORM FIELD CALCULATIONS

CLAIM OF PRIORITY OF PRIOR FILED APPLICATION

This application is a continuation of application having Ser. No. 13/879,841 and a filing date of Oct. 29, 2013, now U.S. Pat. No. 9,933,401, which claims priority to and the benefit of PCT application PCT/US2011/056943, filed on Oct. 19, 2011, which in turn claims priority to the provisional application with Ser. No. 61/394,597, filed on Oct. 19, 2010, and entitled "Air Velocity Meter Based on Smartphone or Tablet PC Interface", all applications of which are hereby incorporated by reference in their entireties.

BACKGROUND OF THE INVENTION

Air velocity meters and indoor quality meters and monitors provide HVAC professionals with just a few of the sample tools that they need in the configuration of ventilation systems or to check the air quality of various workspaces. A number of these devices typically include a handheld device that is tethered to a handheld probe which may or may not have a telescoping portion. One example is disclosed in U.S. Pat. No. 7,788,294, entitled "Method and System for Collecting and Analyzing Environmental Data" assigned to GrayWolf Sensing, Inc. of Shelton, Conn., the teachings of which are incorporated by reference herein in their entirety.

One application that can benefit from the portability of these devices is where there is a desire to minimize and/or eliminate infections acquired by patients when they go into hospitals for treatment. The Centers for Disease Control and Prevention estimates that 5%-10% of hospitalized patients develop a healthcare-associated infection ("HAP'), corresponding to approximately 2 million HAIs (~100,000 deaths) each year in US hospitals. The risk of serious complications due to HAIs is particularly high for patients requiring intensive care. Reducing hospital-acquired infection rates has an estimated economic impact of more than $17 billion per year in US. Starting January 2011, hospitals are required to report hospital-acquired infection rates to Medicare. A new national awards program will recognize teams of critical care professionals, hospital units and healthcare institutions able to successfully reduce or eliminate HAIs.

The focus for prevention has been on minimizing contact-based transmission. Hence, many approaches are to assess and minimize contamination of surfaces and contamination through direct contacts. Airborne transmission is a significant factor that can cause HAIs directly and through deposition on surfaces that, in turn, contribute through contact contamination. Airborne transmission has been traditionally addressed through ventilation and filtration control.

The effectiveness of ventilation systems is directly dependent on the load. These systems are designed, in general, for an average load. However, in places such as waiting rooms load variations—number of people, type of illness, confined space—are significant. Inability of the ventilation system to respond, in real-time, to these load variations can result in HAIs. Variations in contamination level in real-time can occur in other areas in hospitals also (e.g., Operating rooms). Routine breathing by people results in the presence of particles and other similar contaminants into the environment. These, in turn, are easily inhaled by others resulting in an intake of unwanted, problematic species into their system. Undoubtedly, such situations lead to additional infections and illnesses. Admission rooms and waiting rooms of hospitals and clinics are invariably occupied by people having different types and levels of infections. Ironically, such a situation can result in patients in the waiting areas acquiring an infection or disease different from what they had wanted to be cured. There is a substantial need, especially in emerging economies, to implement infection control systems that eliminate the possibility of patients acquiring additional infections from each other without having to invest heavily in infrastructure costs in new hospital construction or the retrofitting of same with legacy air quality measuring and monitoring systems.

Another area that is challenged with data collecting and management and that use dedicated legacy systems is in the agricultural setting. Sensors and data storage devices typically are installed on farm equipment and combines in general, and more specifically at the distal ends close to the seed deposition part of the equipment. Later enhancements in these systems are difficult to retrofit due to each system being developed as a closed loop legacy system. Hence, there is a need to develop flexibility in future data collection systems having remote sensing devices.

SUMMARY OF THE INVENTION

In one example embodiment, a system for measuring at least one parameter in a fluid flow, the measuring system comprising a portable probing device having an extended body portion with a sensor assembly disposed at one end of the probing device configured to measure at least one parameter and the probing member having means for transmitting parameter data therefrom. The sensor assembly is also configured to receive a replaceable pre-calibrated sensor element. The system further includes a handheld communications device having a screen display thereon adapted to receive a set of parameter data from the probing device. The communications device is further adapted to process the parameter data and generate a message when the parameter of the fluid flow exceeds a predefined range. In a related embodiment, the handheld device receives the parameter data either wirelessly or via a wire.

In another example embodiment, a system for measuring at least one parameter in a fluid flow comprises a handheld communications device having a screen display thereon adapted to receive a set of parameter data from a probing accessory coupled thereto. The communications device is adapted to process the parameter data and generate a message when the parameter of the fluid flow exceeds a predefined range. The probing accessory includes a sensor assembly disposed at one end for measuring at least one parameter, the sensor assembly being configured to receive a replaceable pre-calibrated sensor element.

In yet another embodiment, a system for measuring and calibrating a controller used for controlling fluid flow in a selected space comprises a portable probing device having an extended body portion with a sensor assembly disposed at one end of the probing device configured to measure at least one parameter characteristic of the fluid flow. The probing device further including means for transmitting parameter data therefrom. The system further includes a portable communications device having a screen display thereon adapted to receive a set of parameter data from the probing device, said communications device adapted to process the parameter data and generate a message when the parameter of the fluid flow exceeds a predefined range. The controller to be calibrated is coupled to the communications device and is adapted to receive and be responsive to the generated message by changing the fluid flow in the selected space. In a related embodiment, the sensor assembly is configured to include a sensor element selected from the group consisting of a temperature sensor element, humidity sensor element, and pressure sensor element. In a related embodiment, the communications device receives the parameter data either wirelessly or via a wire.

In another related embodiment, a system for improving indoor air quality and air flow within a facility comprises an air quality monitoring system adapted to detect biologically viable and non-biologically viable particles, the air quality monitoring system capable of transmitting a set of air quality data upon request. The system includes a controller adapted to receive the set of air quality data from said monitoring system and analyze the air quality data, said controller further adapted to transmit an instruction to at least change the air quality data. The system further including a ventilation system having at least one air cleansing device and a least one airflow control device, the ventilation system adapted to be responsive to said air quality monitoring system and to said controller to reconfigure the air cleansing device and the airflow control device to change the air quality data within the facility. In a related example embodiment, a low cost wireless probe configured to communicate with a smartphone or a tablet PC would allow healthcare workers to assess daily the effectiveness of hospital or clinic ventilation systems. In a related embodiment, the controller receives the parameter data either wirelessly or via a wire.

In another related embodiment, an apparatus for managing data traffic from remote sensors in agricultural equipment is disclosed that comprises a portable controller adapted to communicate with at least one remote sensor assembly and configured to receive a set of farming parameter data from said at least one remote sensor assembly. The controller is further adapted to process the farming parameter data and provide results to a user. The apparatus further includes a frame configured as a docking station for said controller having disposed thereon at least one control button and a power button. The frame is adapted to receive the portable controller and energizes said power button upon docking said controller in said frame. A major advantage to this embodiment would reduce the number of screens or displays in a farmer's tractor equipment.

BRIEF DESCRIPTION OF THE DRAWINGS

The operation of the invention will become apparent from the following description taken in conjunction with the drawings, in which.

DETAILED DESCRIPTION

Figure 1:
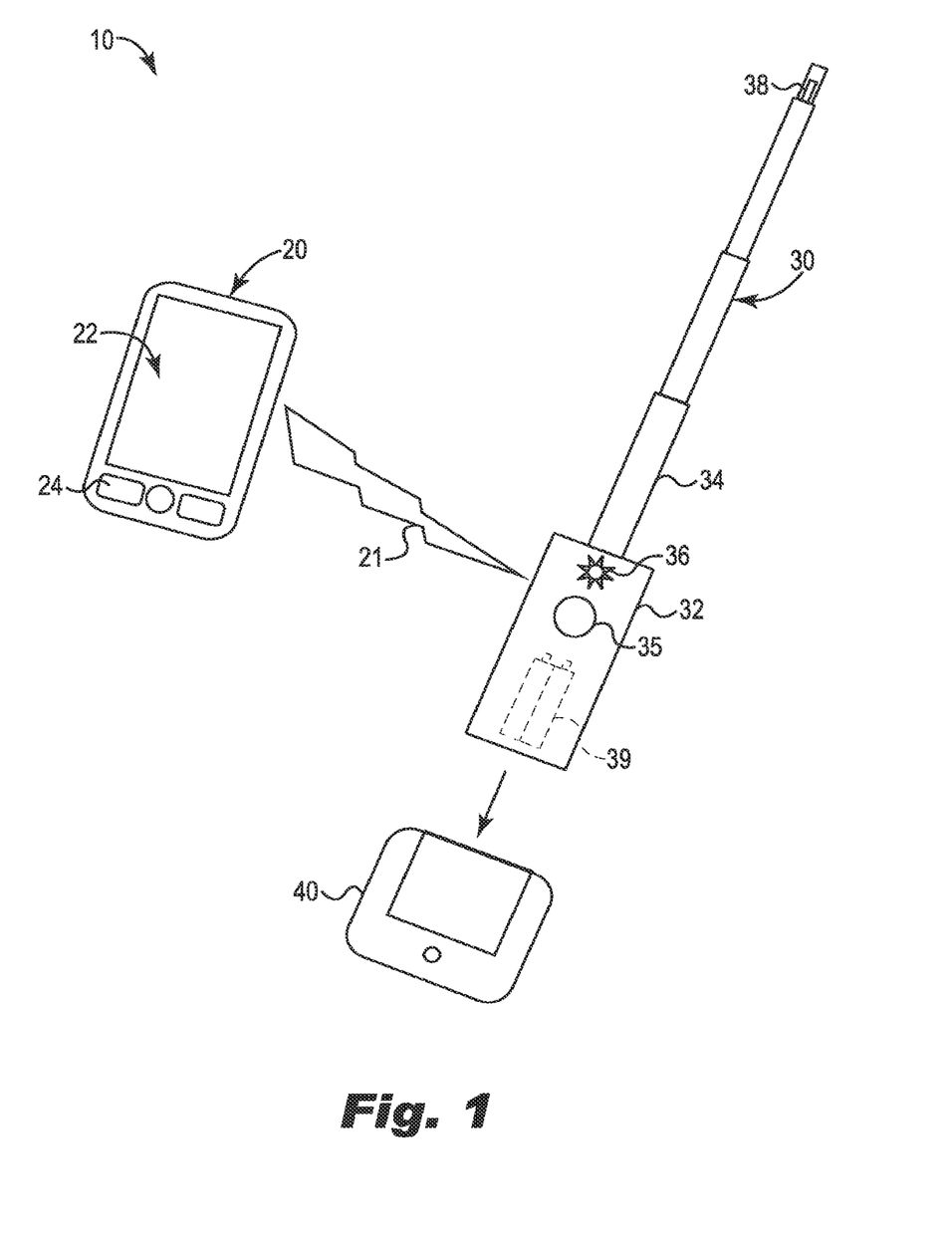
FIG. 1 is a diagram illustrating a smartphone device adapted to communicate with a wireless sensor probe according to the invention.

In accordance with the various embodiment disclosed herein of the invention, it is contemplated that the methodologies and system described are implemented on a general purpose computing device, such as, but not necessarily limited to, a PDA or smartphone or handheld PC, a tablet PC or iPad, a notebook computer, desktops and the like. Referring now to FIG. 1, there is a diagram illustrating an air quality measurement system 10 that includes a smartphone or PDA device 20 adapted to communicate wirelessly 21 (Bluetooth or radio frequency or optically, etc.) with a wireless sensor probe 30 according to one example embodiment the invention. In this example embodiment, system 10 includes a charging station 40 for cordless probe 30. Probe 30 further includes a handle 32, a telescoping antenna 34, a control button or knob or switch 35, an LED user interface or display 36 and rechargeable batteries 39 (lithium or the like). In a related embodiment, the sensors or probes are connected in a hardwire configuration to each other or to the "smart-device" and then the smartdevice communicates out either wirelessly or via cable to other systems.

In this example embodiment, the combination of a smart phone or tablet PC with an air velocity measurement probe creates a useful measurement device for HVAC engineers and air quality management professionals. This will allow a shift from customized instruments with its own display, processor, batteries and a cable connected probe (e.g. TSI, Model 9515/9545/9555), to instruments based on an iPhone or Android platforms or similar based smart phone with a Bluetooth interface with an air velocity probe or indoor air quality probe, which will reduce the cost and create new functionallyfor the customer. A Bluetooth or similar wireless connection between the probe and smart phone allows reading the measurement results in real time. This eliminates a costly cable to the probe and improves the handling and portability. It also provides a powerful computing platform and display for a very low cost to the user. For example, the text to voice engine can announce readings to the user. In addition, the smartphone can be used for many additional purposes (phone, web browser, apps, etc.)

In this example embodiment, using a smart phone or tablet PC eliminates the need for custom designed instruments since smart phone 20 (or a tablet PC) can serve as the user interface. The software (or Application) stores the measurement data and serve as a database and is configurable to create a calibration report on the smartphone display. In a related embodiment, the software (or Application) sends measurement data over the internet, using a telephone, smartphone, netbook or via an internet appliance using a Wi-Fi network.

Measurement data and instrument status can be collected via the internet using a smartphone to provide additional services to the end user. In an example embodiment, the software (Application) provides access to application notes and specifications or connects customers to customer service representatives for improved decision-making. In yet another related embodiment, a GPS/Map feature allows tracking of the work locations. A user input key(s) and LED on the probe would function as a simple interface. In this example embodiment, the user depresses button 35 (see FIG. 1) to initiate measurement and transfer and LED 36 advises user of current status. Probe 30 with replaceable or rechargeable batteries 39 and a USB interface (not shown) is used having same standard charger that most cellphones and smartphones are using. In a related embodiment, a built-in camera in smartphone 20 aides in documentation of calibration locations (pictures or videos could be inserted into calibration reports) and efforts.

In a related embodiment, measurement system 10 reduces (or separates) processing functions normally performed within the sensor probe that is tethered to the main handheld instrument by running the processing functions instead on smartphone 20 (thereby making the probe more of a passive element of measurement system 10). In another related embodiment, probe 30 is designed with an integrated cover, thereby eliminating the need (and cost) for a separate carrying case. In another embodiment, measurement system 10 includes probe 30 with a field replaceable probe tip 38, which helps to eliminate downtime for the customers and reduce shipping costs when having to send the unit to the manufacturer for calibration or verification. By way of example, Model 9515 sold by TSI, Inc., of Shoreview, Minn., is calibrated together with the instrument and the calibration data is stored in the instrument. Using a smartphone based approach, as taught by the various embodiments described herein, allows the calibration data to be stored in the smartphone memory instead.

In a low cost embodiment of system 10, probe tip 38 of probe 30 would only hold the RTD (resistance temperature detector) air velocity sensor and a connector. The amplification and digitization could happen in the antenna or the probe handle. In a related embodiment, probe tips such as probe tip 38 are interchangeable by providing a unique calibration parameter with each tip. New probe tips are sent out calibrated with a calibration ID number. During a one-time setup, a user enters this number into a specific App that would acquire the individual calibration parameter from a manufacturer's server through a secure web interface.

In another related embodiment, a probe 30 is shipped with a bar code label or QR code attached. Using a bar code (or QR) reader App allows reading the code with the camera built into most smartphones.

Figure 2A:
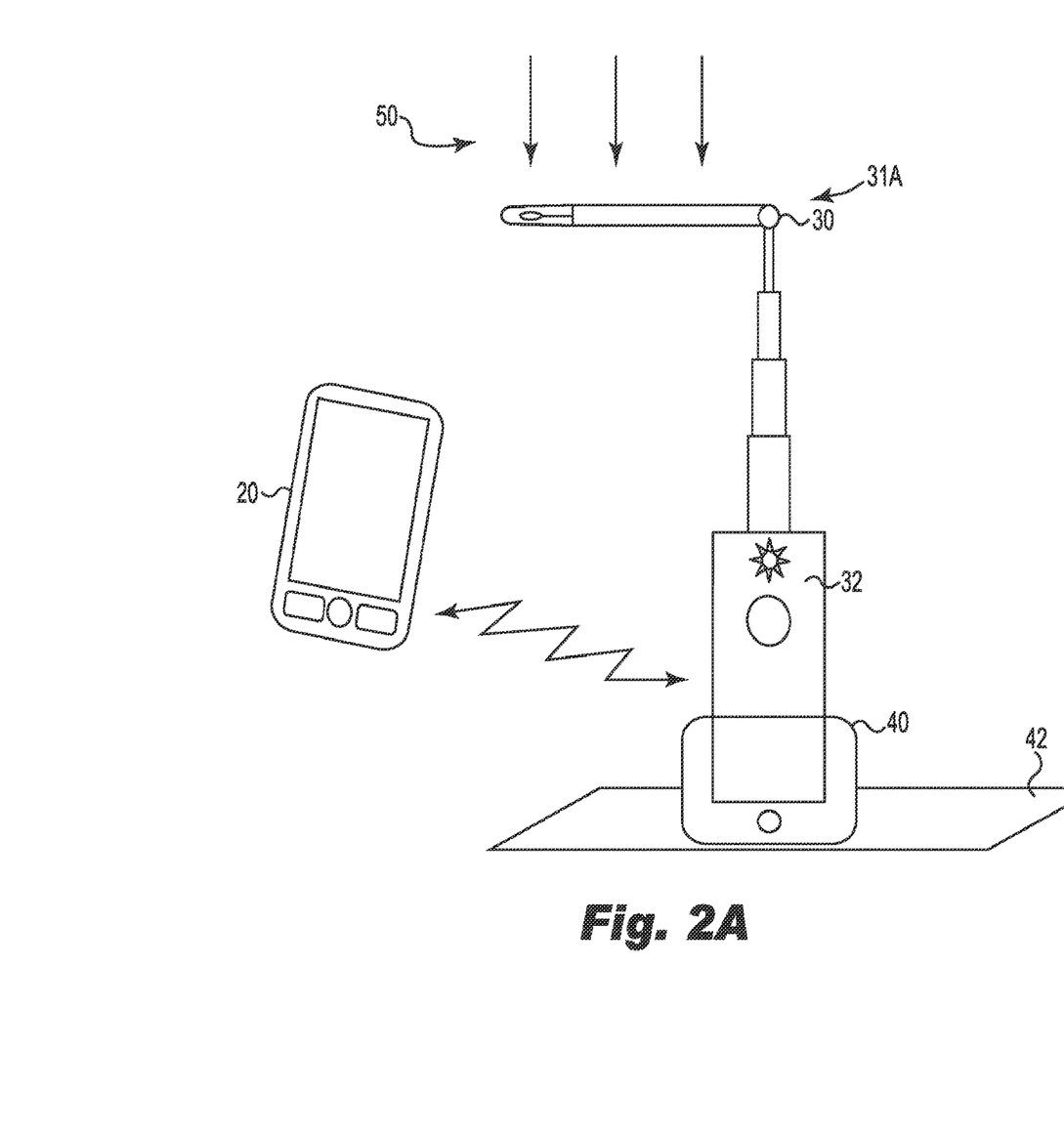
FIGS. 2A-2C illustrate various embodiments of a wireless measurement probe adapted to communicate with a portable controller for use in various applications.
Figure 2B:
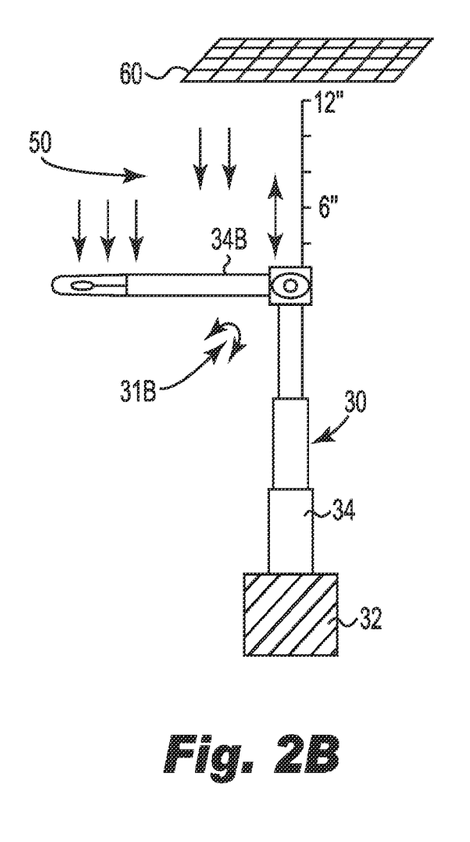
Figure 2C:
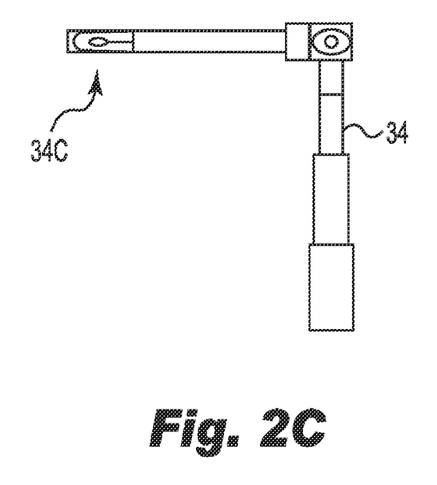

Referring now to FIGS. 2A-2C, there is illustrated various embodiments of a wireless measurement probe 30 adapted to communicate with a protable controller 20 for use in various applications. In FIG. 2A, a separate stand 42 to hold probe 30 for a fume hood or bio safety cabinet calibration makes hands-free measurements possible. Stand 42 includes a ruler or aid to guide users in the correct positioning of probe 30 for the different grid patterns. In this example embodiment, a portion of antenna 34 is bent at joint 31A at a right angle to an air flow 50 being measured.

Referring now to FIGS. 2A-2C, there is illustrated various embodiments of a wireless measurement probe 30 adapted to communicate with a portable controller 20 for use in various applications. In FIG. 2A, a separate stand 42 to hold probe 30 for a fume hood or bio safety cabinet calibration makes hands-free measurements possible. Stand 42 includes a ruler or aid to guide users in the correct positioning of probe 30 for the different grid patterns. In this example embodiment, a portion of antenna 34 is bent at joint 31A at a right angle to an air flow 50 being measured.

Referring now to FIG. 2B, there is illustrated another probe 30 having an antenna portion 34B at a right angle to air flow 50 flowing from air vent or filter 60 (which can also be a HEPA filter). In this example embodiment, a built-in guide 34A, in the form of a simple rod with an inch or metric marking, is added to the probe antenna to facilitate the measurement and spacing between the probe sensor and the HEPA filter (typically 6 or 12 inches for bio safety cabinets or HEPA ceiling filter). In a related embodiment, the sensor portion of the probe is made to be a removable component that is combined with the articulating or pivoting portion of the antenna and made out of plastic or polypropylene to reduce costs.

Figure 3A:
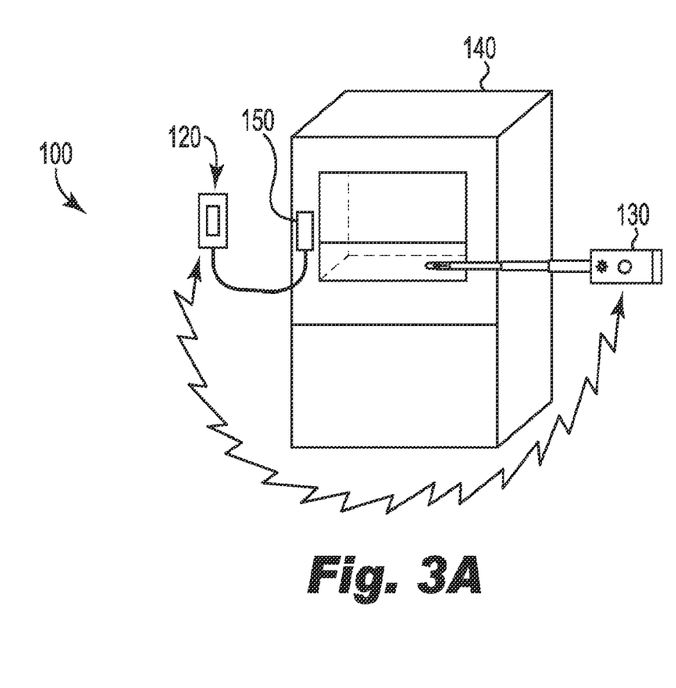
FIGS. 3A-3B illustrate embodiments of systems for calibrating and/or configuring environmental systems using a smartphone to communicate wirelessly with a measurement probe in accordance with the invention.
Figure 3B:
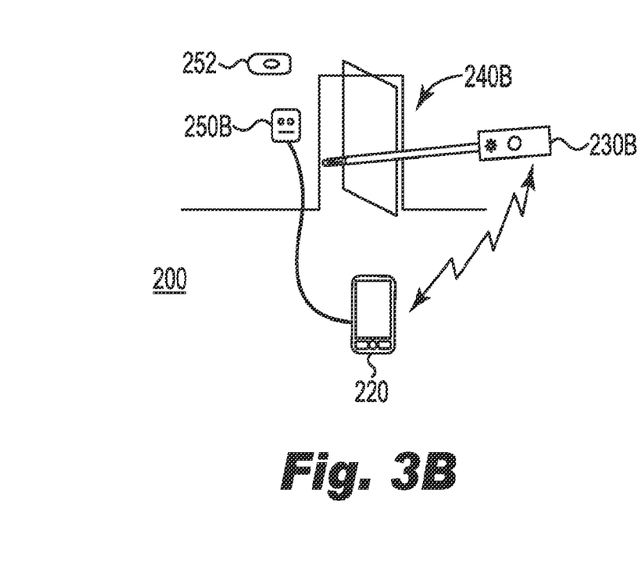

Referring now to FIGS. 3A-3B, there is illustrated various embodiments of measurement and calibration system 100, similar to system 10, for calibrating and/or configuring environmental systems using a smartphone 120 to communicate wirelessly with a measurement probe 130 in accordance with the invention. In this example embodiment, a fume hood 140 includes a fume hood controller/monitor 150 and illustrates probe 130 in an open part of the fume hood. Smartphone 120 communicates with controller 150 via a USB cable and communicates with probe 130 via Bluetooth or RF communication. In this example embodiment, the software (or Application) programmed into smartphone 120 guides the user through a step-by-step process of the measurement and calibration of the fume hood. In this example embodiment, an Android based smartphone features a USB interface that connects to Model FHM10 or FHC50, sold by TSI, Inc. The App is configured to guide through the setup options and generate a setup report that is sent to the manufacturer's server or directly to the customer by email or other form of communication. In a related embodiment, another App is designed to guide a user through certain air flow measurements, such as, but not limited to, duct traverse measurement, fume hood calibration, bio safety calibration, and air flow balancing.

In a related embodiment, multiple wireless or wired probes are configured as an array as a measurement system. In one example, the array is used in a 4×4 fumehood test by having a 4×4 sensor array that takes only 4 measurements instead of 16.

Referring now to FIG. 3B, there is illustrated a method and system for calibrating a room pressure controller monitor system 200 disposed close to of a room 240. In this example embodiment, system 200 includes a smartphone 220 that communicates wirelessly with an air velocity probe 230 and that is coupled to pressure monitor 250 with a USB cable. Pressure monitor 250 is adapted to communicate with a room pressure sensor 252 that is generating readings on an on-demand basis. Smartphone 220 is configured with software that generates a calibration and verification report that allows an HVAC technician to vary the air flow in the ventilation system to ultimately adjust the room pressure.

In yet another related embodiment, an App is provided to could be design for contamination control products for laboratory or pharmaceutical manufacturing operations that utilize optical particle counters (OPCs) for indoor air quality. This would facilitate service checks of installed Remote OPCs (check setup of alarm levels, reading cleaning status, troubleshooting, etc.).

Figure 4:
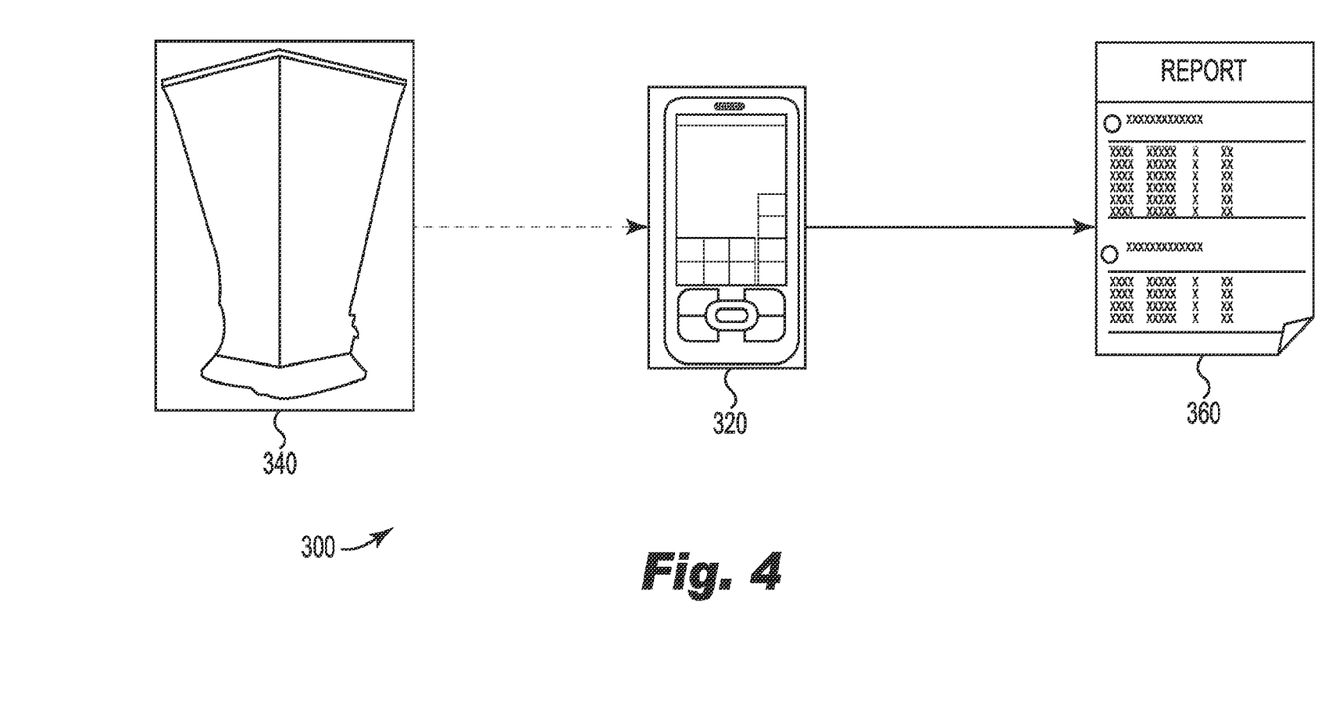
FIG. 4 illustrates an embodiment of air capture hood adapted to communicate with a smartphone accordance with the invention.

Referring now to FIG. 4, there is illustrated an embodiment of a ventilation monitoring system 300 that includes an air capture hood 340 adapted to communicate with a smartphone device 320 in accordance with the invention. Air capture hood 340 provides, via a wireless communication module, air measurement data that is received by smartphone device 320. Device 320 in turn provides the user with a report 360 that can be relayed to an email system or a portable printer for review and for calibration of the vent system measured by capture hood 340.

Figure 5A:
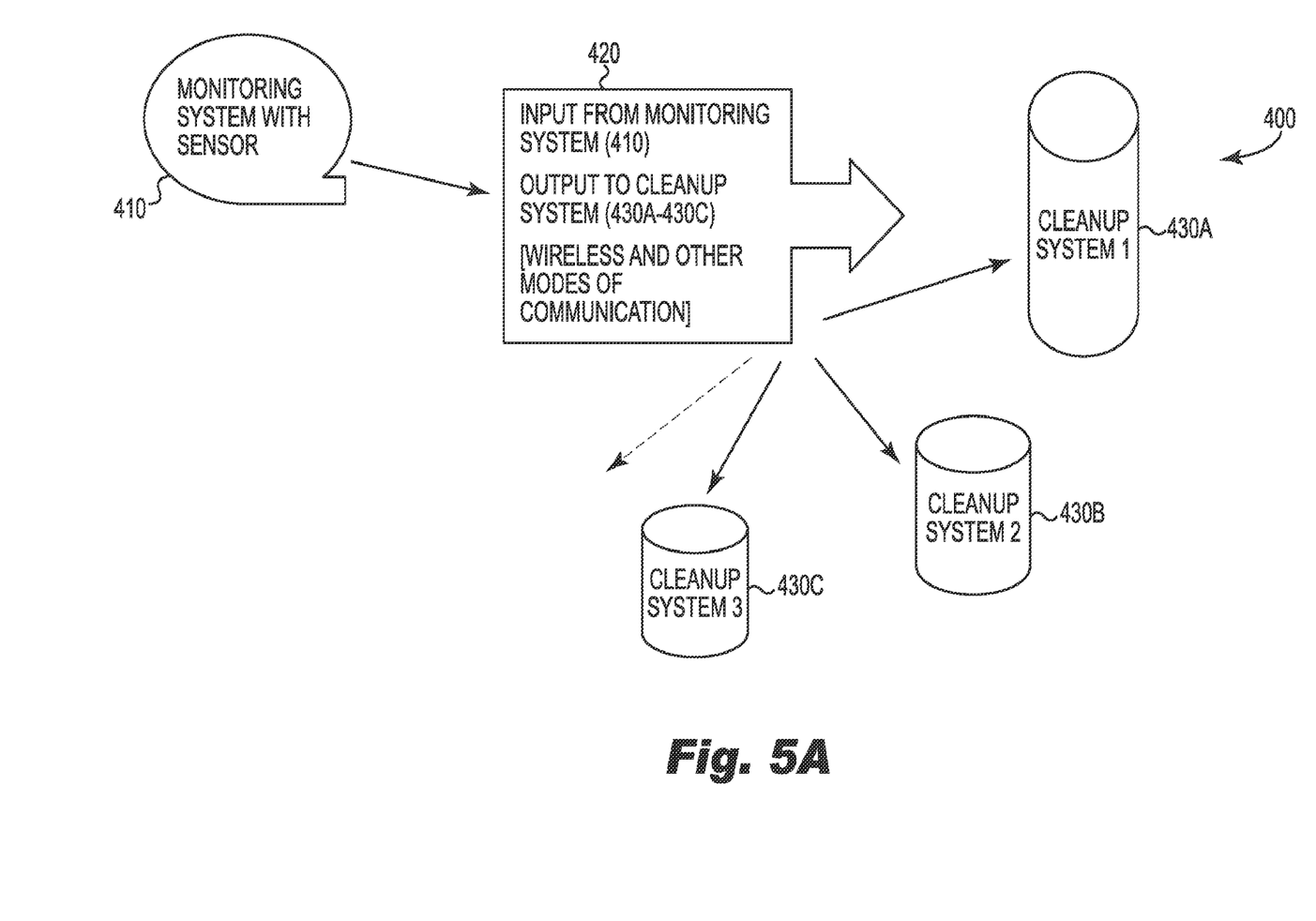
FIGS. 5A-5B illustrate an overall air quality management system and a related portable device in accordance with an embodiment of the invention.

Referring now to FIG. 5A, there is illustrated an overall air quality management system 400 in accordance with an embodiment of the invention that is adapted for use in a facility such as a cleanroom environment or a hospital setting. In a hospital or waiting room setting, minimizing HAIs (healthcare-associated infections) and the spread of other possible infections is accomplished using system 400 due to its ability to respond automatically to potential increases in contaminants. Example of contaminants includes particles, viable particles, virus, bacteria, anesthetic gases and other contaminants.

In this example embodiment, system 400 is configured to respond in real-time, to a predetermined contamination level that is essential to minimizing the spread of disease and infections in the facility. One or more monitoring devices 410 include a sensor selected or configured to sense a particular parameter (temperature, humidity, dust or the like) or contaminant on a real time, continuous basis. Devices 410 are configured to monitor the environmental conditions including one or many of the properties of the contaminants/particles in the environment.

In this example embodiment, system 400 includes a plurality of cleansing or cleanup systems 430A-430C that include but are not limited to ventilation systems with blower fans and filter assemblies (such as HEPA, ionic, dust, water/gel,), irradiation apparatus, vents, baffles, louvers and the like that control or condition the air and the environment. In various example embodiments, system 400 includes distributed system or a central system with distributed ports. System 400 is activated in the wireless mode, in this embodiment, or otherwise.

In this example embodiment, a controller 420 (which is a smartphone, tablet PC or the like) uses a wireless signal output received from monitoring device 410 (or from other similar sensing devices). In this example embodiment, controller 420 is configured to generate an Occupancy Factor signal (based on an App or algorithm previously configured for the selected application) that serves as a trigger signal for activating other devices and controls within system 400 to improve the air quality. The Occupancy Factor is a parameter that can be used to describe the condition of or the load created in a space (room, lab, hospital waiting room, museum, concert hall.). This is influenced by a variety of factors: number of people present, particulate matter (viable and otherwise), temperature, air flow, humidity are some of the factors. Signals generated from monitoring these and similar factors are used to generate the Occupancy Factor in real time.

In a related embodiment, devices 410 are selected to be Hospital Room Pressure Monitors/devices configured to interface with controller 420 with an App specific to guide users (e.g., hospital facility manager) through the monthly pressure and air flow checks in the various rooms. Controlling the air flow and pressure in each room by way of cleansing systems 430 aids in controlling the spread of bacteria and other contaminants to other parts of the hospital that are connected to the same ventilation system. This App then provides a paperless maintenance check record. Results could be sent by email or loaded to the main hospital server or to another remote secure server used by the air quality monitoring company (similar to a remote security monitoring service).

In related embodiments, system 400 is modified to operate in pharmaceutical and medical device cleanroom facilities and semiconductor manufacturing plants requiring high levels of good air quality and warning systems of potential contaminants. In these applications, optical particle counters (OPCs) are strategically placed in the facility and wirelessly communicate biological and non-biological particle data to controller 420, which in turn advises building management that cleansing systems 430 need to be engaged or altered, either manually or automatically via a wireless signal or command from controller 420 to cleansing systems 430. Controller 420 is also configurable to advise management of a production problem in a particular product or drug lot so that quarantine measures can be taken.

In a related embodiment, the form factor of the sensor, blower and filtering device is in one portable device that includes a communication module that is configured to communicate (wired or) wirelessly to a tablet PC, smartphone or a larger central system. An advantage of a portable device would be to place it in a room (or one in each room in a portable system) and begin to generate air quality or occupancy factor data (and associated signals) that is picked by up the tablet PC or smartphone.

Figure 5B:
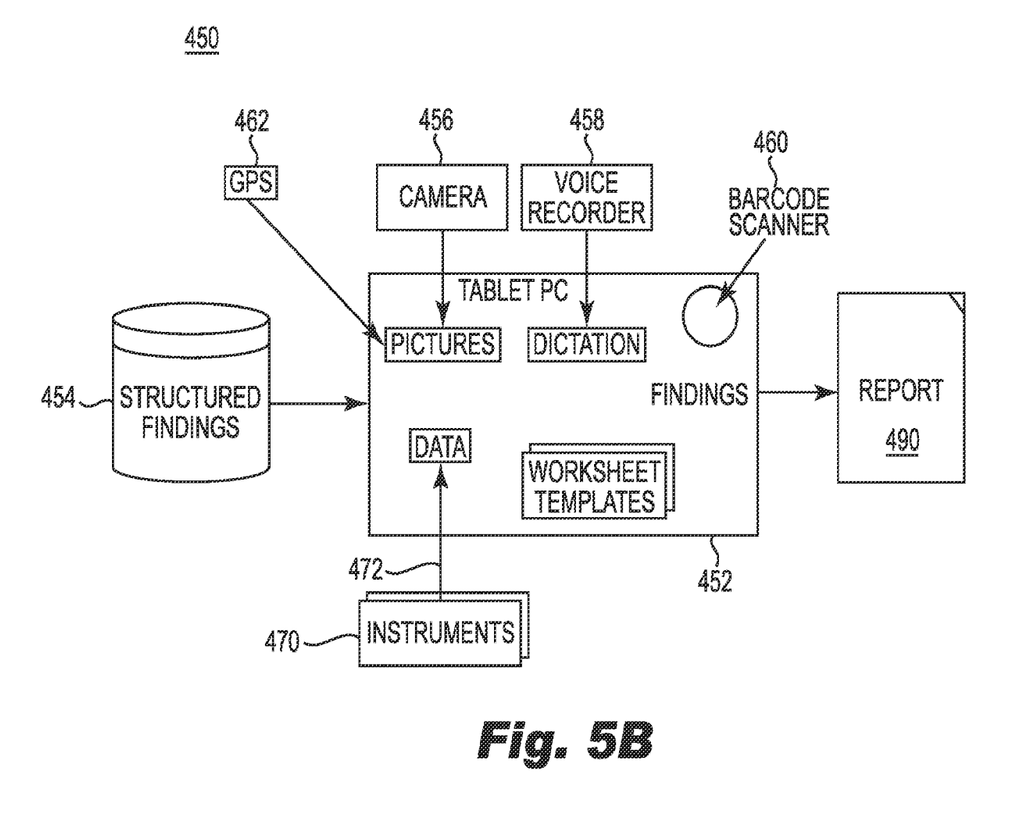

Referring now more specifically to FIG. 5B, there is illustrated an indoor air quality apparatus 450 that uses a tablet PC or smartphone 452 to communicate with instruments 470, via a wired or wireless channel 472 to generate a report 490 after receiving a set of data from various input devices. In this example embodiment, device 452 is configured to receive a set of data or structured findings 454, findings can be supplemented with photos via camera 456, voice reports or comments via microphone 458 and or bar code data via barcode reader 460 and optional locational data using a GPS App 462 and detector. In a related embodiment, device 452 is configured with worksheet templates to facilitate report preparation. In one example embodiment, an App is generated that uses forms and guidelines for air quality metrics. An example of such metrics is outlined in the Indoor Air Quality Tools Guidance Document, dated February 2003, Version 2.0 (128 pages; www.ucop.edu/riskmgt/ehs/documents/indoor_airquality.pdf), the contents of which is incorporated by reference in its entirety.

Figure 6:
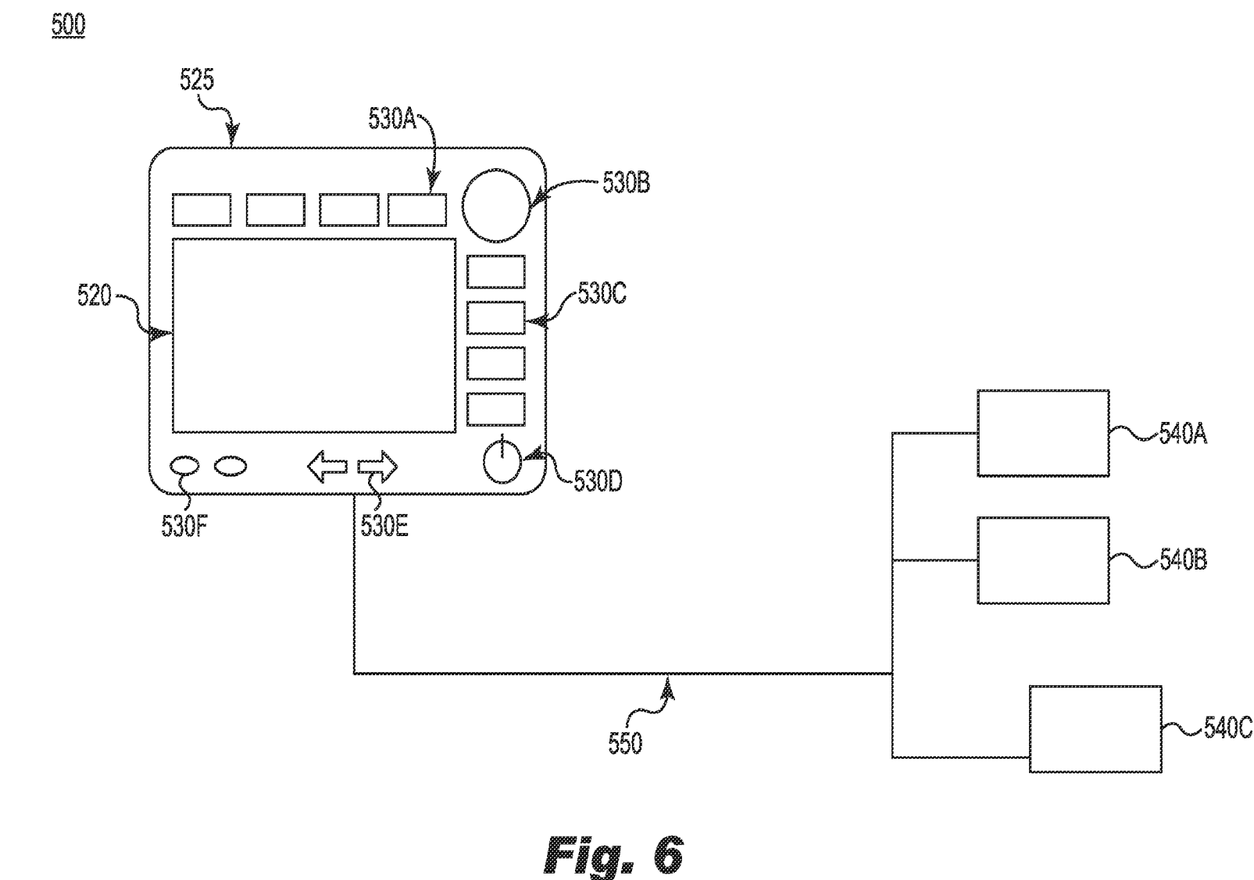
FIG. 6 illustrates a remote sensing and data gathering system incorporating a tablet PC adapted to communicate with other remote sensors in accordance with an embodiment of the invention.

Referring now to FIG. 6, there is illustrated a remote sensing and data gathering system 500 incorporating a tablet PC 520 adapted to communicate wired or wirelessly via channel 550 via a frame 525 with one or more remote sensors 540A-540C in accordance with various embodiments of the invention. As technology continues to penetrate the world of farming, equipment operators require high-resolution color displays coupled with easy-to-use, ergonomically designed controls. Thus far, agricultural equipment vendors have provided dedicated terminals to support each of their various applications. Consequently, as the number of these dedicated terminals in the farm tractor or combine has proliferated, the concept of an ISOBUS-Virtual Terminal that supports multiple applications has appeared.

Meanwhile, tablet computers have ushered in a new wave of computing power in a form factor that adapts well to the virtual terminal, such as communications device 520. Manufacturers, including Motorola and Panasonic have recently begun to introduce ruggedized versions of tablet computers such as tablet PC 520. Although these may be durable enough for farming applications, these tablet PCs still lack the ergonomic controls incorporated in custom virtual terminals. The example embodiments described herein will solve this deficiency by providing controller frame 525 around a COTS (Commercial Off The Shelf) tablet PC 520. In this example embodiment, frame 525 includes a set of soft keys 530A, a control knob 530B, another set of soft keys 530C, a power button 530D, dedicated keys 530E and status indicators 530F. In a related embodiment, a smartphone is tethered to controller frame 525 via a USB cable to facilitate use of the controllers while the smartphone or tablet PC is used for the wireless communications and access to the internet or WiFi network or some other cloud computing network. In one example embodiment, remote sensors 540A-540C are seeding assemblies with sensors thereon. In another example embodiment, remote sensors 540A-540C are fertilizing assemblies with position sensors thereon. In yet another example embodiment, remote sensors or assemblies 540A-540C are chemical treating devices. In this example embodiment, communications channel 550 is a wired connection. In a related embodiment, channel 550 is a wireless protocol such as RF or Bluetooth.

Some virtual terminals that have been offered to date have consolidated a number of controllers in the tractor or combine cab, however they are expensive and limited in functionality. The various advantages of the various embodiments described herein of the controller frame 525 and tablet PC 520 combination include, but are not limited to: the farmer can to flip to other smart applications while in the tractor such as viewing email, checking the weather, browsing the farm report on the web, viewing his field map, observing his GPS coordinates, and many other functions in real time. The true cost of the virtual terminal is reduced as controller 520 is also used as a general purpose tablet PC when the tractor is not being used as controller 520 is decoupled from frame 525. The virtual terminal would continue to take advantage of increasing performance and functionality as price-points fall.

In this example embodiment, controller frame 525 is a hardware control "frame" that contains the custom controls shown in FIG. 6 as well as an ISOBUS-compatible application for the tablet PC. The tablet PC or controller 520 is removable to serve other purposes when not in use within controller frame 525. Controller 520 is configured to include an ISOBUS 11783-compatible application that supports the underlying tablet PCs (i.e. iPad, Android) or netbooks.

The following patents that relate to similar devices of interest are herein incorporated by reference in their entirety and constitute part of the disclosure herein: U.S. Pat. Nos. 6,705,158; 7,305,327; 7,788,294. An example of a nanofiber sensor that can be used with the various embodiments described herein is disclosed in U.S. Patent Publication 2010/0043529, which is incorporated by reference in its entirety.

It is contemplated that the method according to the present disclosure may be used in a variety of different spaces that environmental monitoring would be of use. Typically, the method according to the present disclosure would be useful in any location or space where it is desirable to maintain certain environmental conditions. Some examples include hospitals, restaurants, grocery stores or other retail space, office buildings, science labs, museums, etc.

Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

What is claimed is:

1. An air quality measurement device for measuring at least one parameter of a set of parameters in a fluid flow, the measuring device comprising:
   a smart handheld communications and processing device having a screen display thereon and a smart device operating system and a downloaded software application program disposed in a smart device housing, the smart device configured to wirelessly transmit and receive data in real time with local and remote wireless networks, the smart device adapted to wirelessly receive in real time the set of parameter data from a passive handheld probing accessory wirelessly couplable thereto, said smart device operating system and software application program adapted to process the at least one parameter data in real time on a user initiated measurement, wherein the handheld probing accessory includes a sensor assembly disposed at one end of the handheld probing accessory for measuring the at least one parameter.

2. The air quality measurement device of claim 1, wherein the software program of the smart device is configured to generate measurement data and a calibration report for an apparatus being measured.

3. The air quality measurement device of claim 1, wherein the software application program includes applications to guide a user through any of air flow measurements, duct traverse measurement, fume hood calibration, bio safety calibration and air flow balancing.

4. The system of claim 1, wherein the sensor assembly is configured to include a sensor element selected from the group consisting of a temperature sensor element, a humidity sensor element, and a pressure sensor element.

5. An air quality measurement system for measuring and calibrating a controller used for controlling fluid flow in a selected space comprising:
   a handheld probing device having an extended or telescoping body portion with a sensor assembly disposed at one end of the handheld probing device configured to measure at least one parameter characteristic or data of the fluid flow, the handheld probing device having a user interface thereon configured for a user to initiate measurement of the at least one parameter and to passively and wirelessly in real time transmit parameter data therefrom; and
   a smart handheld communications and processing device having a screen display thereon and a smart device operating system and a downloaded software application program disposed in a smart device housing, the smart device configured to wirelessly transmit and receive data in real time with local and remote wireless networks, the smart device adapted to wirelessly receive in real time a set of parameter data from the handheld probing device upon the user initiating the measurement, said smart device operating system and software application program adapted to process and monitor the parameter data, and wherein the controller is wirelessly coupled to the smart handheld communications and processing device and is adapted to receive and be responsive by changing the fluid flow in the selected space to adjust system balance.

6. The system of claim 5, wherein the sensor assembly is configured to include a sensor element selected from the group consisting of a temperature sensor element, a humidity sensor element, and a pressure sensor element.

7. A system for improving indoor air quality and air flow within a facility comprising:
- an air capture or flow hood adapted to measure air flow in a ventilation system and generate air measurement data, the air measurement data being wirelessly transmitted upon request initiated by a user;
- a smart handheld communications and processing controller having a smart device operating system and a downloaded software application program disposed in a smart device housing, the smart handheld controller configured to wirelessly transmit and receive data in real time with local and remote wireless networks, the smart handheld controller adapted to wirelessly receive a set of air quality data directly from said ventilation system and analyze the air quality data, upon the user initiated request said smart handheld communications and processing controller further adapted to wirelessly transmit an instruction to at least calibrate the ventilation system, wherein the software application program includes applications to guide the user through any of air flow measurements, duct traverse measurement, bio safety calibration and air flow balancing.

8. The system of claim 7 wherein the air quality monitoring system further includes at least one sensor to measure a desired parameter in the facility, the parameter selected from the group consisting of temperature, pressure, humidity, air velocity, and carbon dioxide.

9. The system of claim 7 wherein the handheld controller receives air quality data from the air capture hood through a wireless protocol.

* * * * *